United States Patent [19]

Summer

[11] Patent Number: 5,899,694
[45] Date of Patent: May 4, 1999

[54] GINGIVAL RETRACTION APPARATUS AND METHOD

[76] Inventor: John Summer, 9601 NW. Leahy #305, Portland, Oreg. 97229

[21] Appl. No.: 09/027,442

[22] Filed: Feb. 20, 1998

[51] Int. Cl.⁶ ....................................................... A61C 5/14
[52] U.S. Cl. ................................................................ 433/136
[58] Field of Search ............................................. 433/136

[56] References Cited

U.S. PATENT DOCUMENTS

| | | | |
|---|---|---|---|
| 4,321,038 | 3/1982 | Porteous | 433/136 |
| 4,465,462 | 8/1984 | Ticknor | 433/136 |
| 4,522,593 | 6/1985 | Fischer | 433/136 |
| 4,871,311 | 10/1989 | Hagne | 433/136 |
| 4,892,482 | 1/1990 | Lococo | 433/136 |
| 5,358,403 | 10/1994 | Groth | 433/136 |
| 5,480,303 | 1/1996 | Groth | 433/136 |
| 5,540,588 | 7/1996 | Earle | 433/136 |

FOREIGN PATENT DOCUMENTS 3122834  12/1982  Germany ................................ 433/136

*Primary Examiner*—John J. Wilson
*Attorney, Agent, or Firm*—Klarquist Sparkman Campbell Leigh & Whinston, LLP

[57] ABSTRACT

A loop of cord, projecting out from one end of an elongate sleeve is placed around the base of a tooth and closed. In one preferred form, the cord includes elastic material so that, as the loop is closed around the tooth, the contractile force exerted by the stretched elastic cord around the circumference of the tooth at a part of the tooth which tapers toward the root tends to seat the cord apically (toward the apex of the root). The self-seating tendency of this loop of elastic cord as it is tightened around the base of a tooth more effectively separates the gingival tissues from the base of the tooth. As a result, good clean dry access to the margins of a crown or inlay is provided. In one form, the sleeve is of a heat shrinkable material and is heat shrunk to frictionally engage the cord.

19 Claims, 4 Drawing Sheets

GINGIVAL RETRACTION APPARATUS AND METHOD

FIELD OF THE INVENTION

This invention relates to the methods and apparatus employed by dentists to retract gingival tissues from around the base of a tooth, such as a tooth which has been prepared by drilling or other means to receive a dental restoration, such as a crown or inlay.

BACKGROUND AND PRIOR ART

One of the most important and most difficult procedures in the process of a dentist making a crown or inlay is retracting the gingival tissues in order to be able to obtain an accurate impression of the margins of the crown or inlay which often lie in the sulcus, the narrow groove between the base of the tooth and the surrounding gingival tissues. In taking the impression for a crown or inlay, the dentist must record not only the margin but also the area beyond the margin so that the laboratory can assess the angle of emergence of the tooth from the root and can continue that angle in the contour of the crown or inlay for optimal smoothness of the margin and health of the tissues near the margin. The area beyond the margin often lies at the bottom of the sulcus, a location which is particularly narrow and difficult to record accurately with impression material.

In order to better record the area of the tooth bordering the bottom of the gingival sulcus with impression material, dentists have traditionally used a length of string, called retraction cord or thread, which they push down into the sulcus. The pressure of the cord in the sulcus on the tissues lining the sulcus as well as the hemostatic or astringent medicaments which may be carried by the cord aid in stopping bleeding, shrinking the tissues of the gingival sulcus, and mechanically widening the gingival sulcus in order to allow the dentist to more accurately record the base of the tooth bordered by the gingival sulcus.

U.S. Pat. Nos. 4,321,038; 4,522,593; 4,465,462; 4,871,311; 4,892,482; and 5,540,588 are examples of prior art relating to retraction of gingival tissues.

One disadvantage of all these prior art retraction cords, as these references are presently understood, is that they are supplied in lengths which have to be wrapped around a tooth and then mechanically seated into the base of the sulcus one area at a time with gingival packing instruments. The mechanical seating is time consuming and often traumatic to the tissues under the area of cord which is being packed as well as painful to the patient. The gingival packing instrument often slips off the cord and injures the gingival tissue. Furthermore, dentists frequently have difficulty getting the cord to stay down in the bottom of the sulcus after it has been packed down.

U.S. Pat. Nos. 5,358,403 and 5,480,303 to Groth illustrate devices for applying gingival retraction cord to a tooth. In the '403 patent, a loop of gingival retraction cord is formed with the free ends of the cord being held, as by a threaded plug, in the end of an elongated handle. The loop is placed around the tooth and the handle is twisted to, in turn, twist the gingival retraction cord and tighten the loop around the tooth. A packing tool is then used to urge the retraction cord into the base of the sulcus. In the '303 patent, the retraction cord has a loop extending outwardly from one end of a barrel shaped applicator, with the free ends of the retraction cord projecting outwardly from the opposite end of the applicator. The loop is placed around a tooth, with the free ends of the cord being pulled to reduce the size of the loop. The free end of the loop also passes through a lock which is pivoted to the barrel. The lock is twisted to engage the retraction cord at the location where the retraction cord passes from the barrel to the lock to prevent sliding of the retraction cord. Thereafter, the applicator is twisted so as to twist the loop of the retraction cord and tighten the loop against the tooth. A packing tool is then used to force or pack the gingival cord into the base of the sulcus.

These retraction cord applicators suffer from a number of disadvantages. For example, the pressure applied to the tooth and gingival tissues arising from twisting the cord is difficult to control. The difference between having the retraction cord in a closed but untightened state which applies no pressure around the circumference of the tooth and having the retraction cord in a twisted, tightened state to apply pressure around the circumference of the tooth may be only a millimeter or two. Further twisting the cord another millimeter or two may create too much pressure on the cord and against the gingival tissues. In addition, the applicators of these two Groth patents are relatively bulky, making them inconvenient to use during dental procedures. Moreover, packing tools which can traumatize the gums are still required to pack the retraction cord into the base of the sulcus.

Therefore, a need exists for an improved gingival retraction apparatus and method.

SUMMARY OF THE INVENTION

In accordance with one embodiment of the present invention, an apparatus for retracting the gingival tissues from around the base of a tooth includes a loop formed of a gingival retraction thread or cord. The loop has a first loop portion and a second tail portion, with the second tail portion including at least one free end of the gingival retraction cord. By pulling on the free end or ends of the cord, the cross-sectional dimension of the loop is reduced when the loop is placed around the tooth. A loop retainer, which is preferably of a one piece monolithic construction, frictionally engages the thread with the loop retainer being operable to retain the loop portion in the shape of a loop while permitting the free end or ends of the cord to be pulled to reduce the cross-sectional dimension of the loop. In accordance with this embodiment of the invention, a mechanically simple apparatus is provided consisting of two unitary parts, namely the loop retainer and the cord.

More specifically, the loop retainer, in one form, comprises an elongated sleeve having an internally axially extending passageway which is sized to receive and frictionally engage at least a portion of the cord passing through the passageway. The sleeve maintains the loop at the desired size or cross-sectional dimension following the pulling of the end or ends of the loop.

In a specifically preferred embodiment, the sleeve is of a heat shrinkable material and is heat shrunk to size the interior wall or passageway of the sleeve to compress against and frictionally engage the gingival retraction cord.

In accordance with another preferred embodiment, the gingival retraction cord is preferably an elastic material. By elastic material, it is meant a material which is capable of being stretched sufficiently to create a biasing force against the base of a tooth which urges the stretched loop into the sulcus. Most preferably, the elastic material is capable of being stretched in length at least five percent and more preferably at least ten percent, with a material that is stretchable in length at least about fifty percent being specifically preferred. The use of an elastic material for retracting gingival tissues is extremely beneficial. For example, as a loop of elastic cord is closed around a tooth, an inwardly directed contractile force is exerted by the stretched elastic cord around the circumference of the base of the tooth. At this location, a typical tooth tapers (reduces in circumference) toward the apex of the root. As a result, the gingival retraction cord, when the loop is tightened and stretched, tends to automatically move into the base of the sulcus and seat the cord apically (toward the apex of the root). The self-seating tendency of an elastic loop of gingival retraction material as it is tightened around the base of a tooth more effectively separates the gingival tissue from the base of the tooth. As a result, good, clean, dry access to the margins of the crown or inlay is provided. Furthermore, this self-seating tendency virtually eliminates the need for cord packing tools to achieve the desired retraction of the gingival tissues and results in less trauma to these tissues.

The gingival retraction cord may be soaked or otherwise impregnated or carry medicaments such as astringents, antiseptics, antibiotics, hemostyptics or other solutions or medications for the purpose of applying them to the sulcus.

Apart from the particular form of applicator that is employed, the use of elastic gingival retraction material is advantageous. In addition, apart from the use of elastic gingival retraction material, an applicator in accordance with my invention also offers many advantages over known applicators. My invention also relates to methods for retracting the gingival tissues from around the base of a tooth.

In one specific form, the method includes the step of placing a loop of elastic gingival retraction material around the tooth and tightening the loop to close the loop. This stretches the elastic gingival retraction material to generate an inwardly directed force against the tooth, which results in the retraction material being urged into the sulcus to cause retraction of the gingival material. The elastic material thus assists in seating the gingival retraction material in the sulcus at the base of the tooth. Most preferably, the elastic material is stretched around the entire circumference of the tooth so as to provide a uniformly inwardly directed force against the entire periphery of the tooth.

In another more specific embodiment of my method, a loop of gingival retraction cord or material passes through an elongated sleeve and is frictionally engaged by the walls of the sleeve to resist sliding through the sleeve following tightening of the loop to the desired size.

The gingival retraction device may be formed by providing an elongated sleeve with an elongated sleeve passageway. A gingival retraction cord is positioned within the sleeve passageway, with a loop portion of the cord extending from a first end of the sleeve and a tail portion of the cord extending from a second end of the sleeve. The cross-sectional dimension of the passageway through the sleeve is reduced to restrict the ease at which the cord may be pulled through the sleeve and correspondingly resist changes in the dimension of the loop. Consequently, upon tightening the loop around the tooth, the loop remains in a tightened condition until the cord is removed. In a specifically preferred approach, the sleeve is made of a heat shrinkable material which is heat shrunk to reduce the cross-sectional dimension of the passageway and restrict the ease at which the cord may be pulled through the sleeve.

It is an object of this invention to provide an improved way of retracting the gingival tissues from around the base of a tooth, for example a tooth which has been prepared for a dental restoration, such as a crown or inlay.

It is a further object of this invention to provide a loop of gingival retraction cord which can be easily closed around the base of a tooth and retained in a closed state so that it provides light steady tension all around the circumference of the tooth.

It is a further object of this invention to provide a loop of gingival retraction cord and a means for closing it and retaining it closed which is simple to use and inexpensive to produce so that it may be provided as a disposable item.

The present invention relates to these features, advantages and objects individually as well as collectively. These and other objects, features and advantages of the present invention will be apparent from the following description and drawings.

DETAILED DESCRIPTION OF PREFERRED EMBODIMENTS

Figure 1:
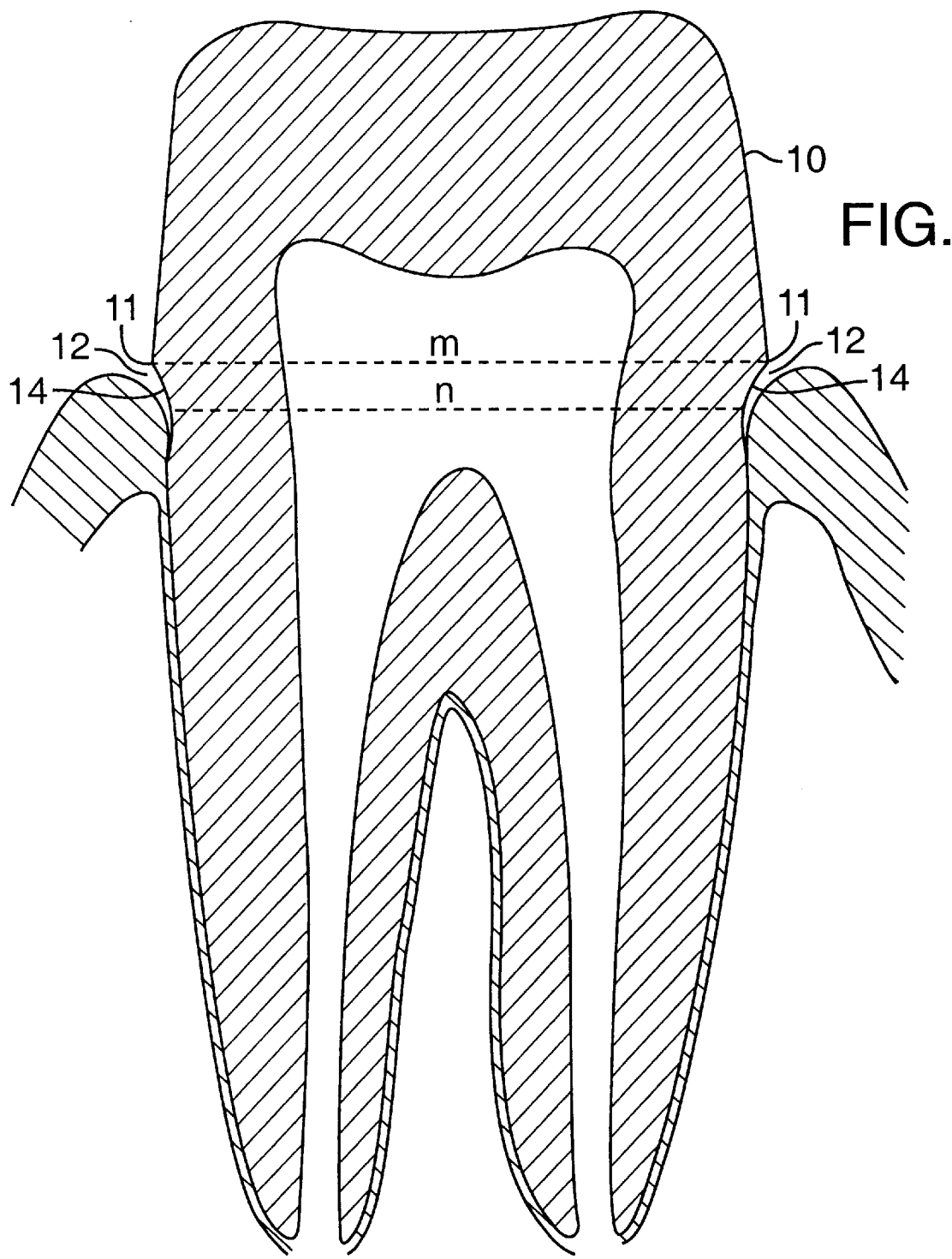
FIG. 1 shows in vertical cross section a tooth which has been prepared for a crown as well as the gingival tissues surrounding it.

In FIG. 1, a tooth 10 is shown that has been drilled down or otherwise prepared by a dentist for receiving an artificial crown. The margin 11 of the crown preparation are the parts of the preparation which are located farthest apically (in the direction of the apex of the root). Neck 14 of a typical tooth, which is located closer to the apex of the root than margin 11, has a reduced circumference n relative to the circumference m of the tooth at the margin of the preparation. Sulcus 12 is the narrow groove between the neck of the tooth and the surrounding gingival tissue. The narrowness of the base of the sulcus makes it difficult to accurately record the part of the tooth lying within the sulcus, such as with dental impression material. Furthermore, the sulcus often fills with blood or saliva, making it even more difficult to fill the sulcus with impression material.

Figure 2:
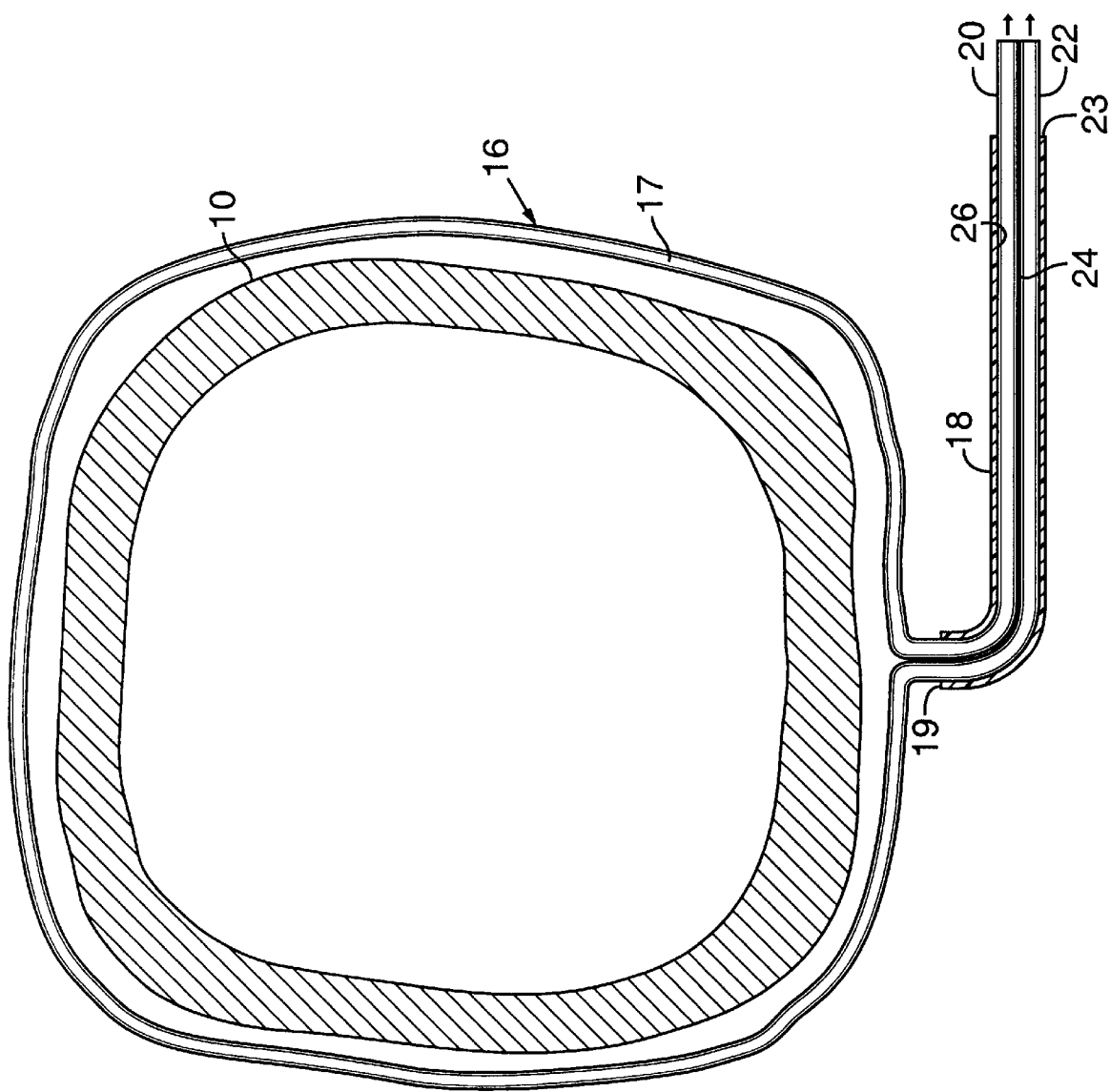
FIG. 2 is a top plan view of the tooth of FIG. 1 surrounded by an elastic gingival retraction loop in accordance with one embodiment of the invention, which has not yet been closed around the base of the tooth.
Figure 5:
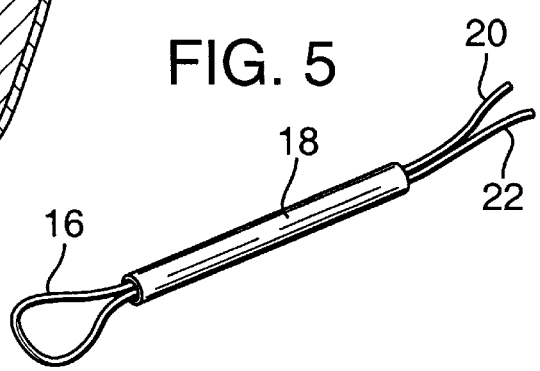
FIG. 5 is a perspective view of the embodiment of FIGS. 2 and 3.

FIG. 2 shows a top plan of the tooth illustrated in FIG. 1, like elements being indicated by like numbers. An elastic gingival retraction loop 16 is shown in the passive (unstretched) state fitting loosely around tooth 10. It can be seen (see also FIG. 5) that the illustrated loop is formed of an elongated material 17, such as from a cord which is doubled back on itself to form the loop. A retainer is used to retain the cord in a loop shape. The loop retainer may take other forms, but in the illustrated embodiment comprises a monolithic elongated tube or sleeve 18 having first and second ends 19, 23 and a hollow interior 24. The sleeve has an interior wall surface 26 which bounds a cord receiving passageway extending axially through the sleeve and between ends 19 and 23. The loop 16 projects outwardly from the end 19 of sleeve 18 located closest to the tooth. Typically, when initially positioned, the loop 16 is larger in circumference or cross-sectional dimension than the tooth by one-quarter inch or more so that it can be easily slipped over the tooth. The free ends 20, 22 of cord 17 form a tail which projects outwardly from the end 23 of the sleeve 18 which is farthest from the tooth. The arrows at the cord terminations 20, 22 represent the direction in which those tail portions are pulled by the dentist or other user in order to tighten the elastic gingival retraction loop 16 around the tooth.

In the illustrated embodiment, the cord retainer, in this case sleeve 18, is and of one-piece and is composed of a heat shrinkable material, such as of a heat shrink plastic. During manufacture, the cord is placed into the internal elongated axially extending passageway defined by the sleeve before the sleeve is shrunk around the cord. The sleeve is sized in cross-sectional dimension relative to the cross-sectional dimension of the cord so that it will shrink sufficiently to provide an internal passageway which is sized to compress against the cord. The interior wall 26 bounding the passageway provides enough friction between the cord and wall so that the cord cannot spontaneously or readily slip through the internal passageway without being pulled through the passageway by the dentist or other user. This friction thus locks the cord and freezes the cross-sectional dimension of the loop after it has been tightened around the tooth.

As a specific example, sleeve 18 may be of a two to three inch length of a flexible heat shrink plastic, such as of a polyolefine material, with ST-301 tubing from the 3M Company being a specific example. In prototypes manufactured to date, tubing with an unshrunk diameter of one-eighth inch and one-thirty second inch have been used. In addition, the retraction material may have varying cross-sections and configurations. Although not limited to a specific type of cord or retraction material, in suitable prototypes manufactured to date, an elastic sewing thread from Rhode Island Textile Company of Providence, R.I. has been used. This specific cord is made with an outer braided cover surrounding a central core, which appears to be of rubber. Unstretched cord of this type from this company having a diameter of one-thirty second inch was used in prototypes with the one-eighth inch diameter 3M Company. Unstretched cord from this company observed to be about one-sixty-fourth to about three-one twenty-eighth inch was used in prototypes with the three-thirty second inch diameter tubing from 3M Company.

In general, a suitable elastic cord is one which is capable of stretching in length from five percent to seventy-five percent. The percent stretch is determined by the following formula:

$$\text{percent stretch} = \left( \frac{[\text{stretched length} - \text{unstretched length}]}{[\text{untreated length}]} \right) \times 100$$

More preferably, the elastic cord is stretchable at least ten percent beyond its relaxed length, with a stretchability of at least about fifty percent being specifically preferred.

The cord material is selected to have a configuration and elasticity which encourages the cord, when tightened, to automatically slide along the tooth and into the sulcus. With this approach, the need for using cord compaction tools is virtually eliminated. In tests to date, the applicant has repeatedly seated the loop in the sulcus by simply tightening the loop without using any packing tools. However, it is possible that a tooth could have a configuration making it helpful to use such tools.

Figure 3:
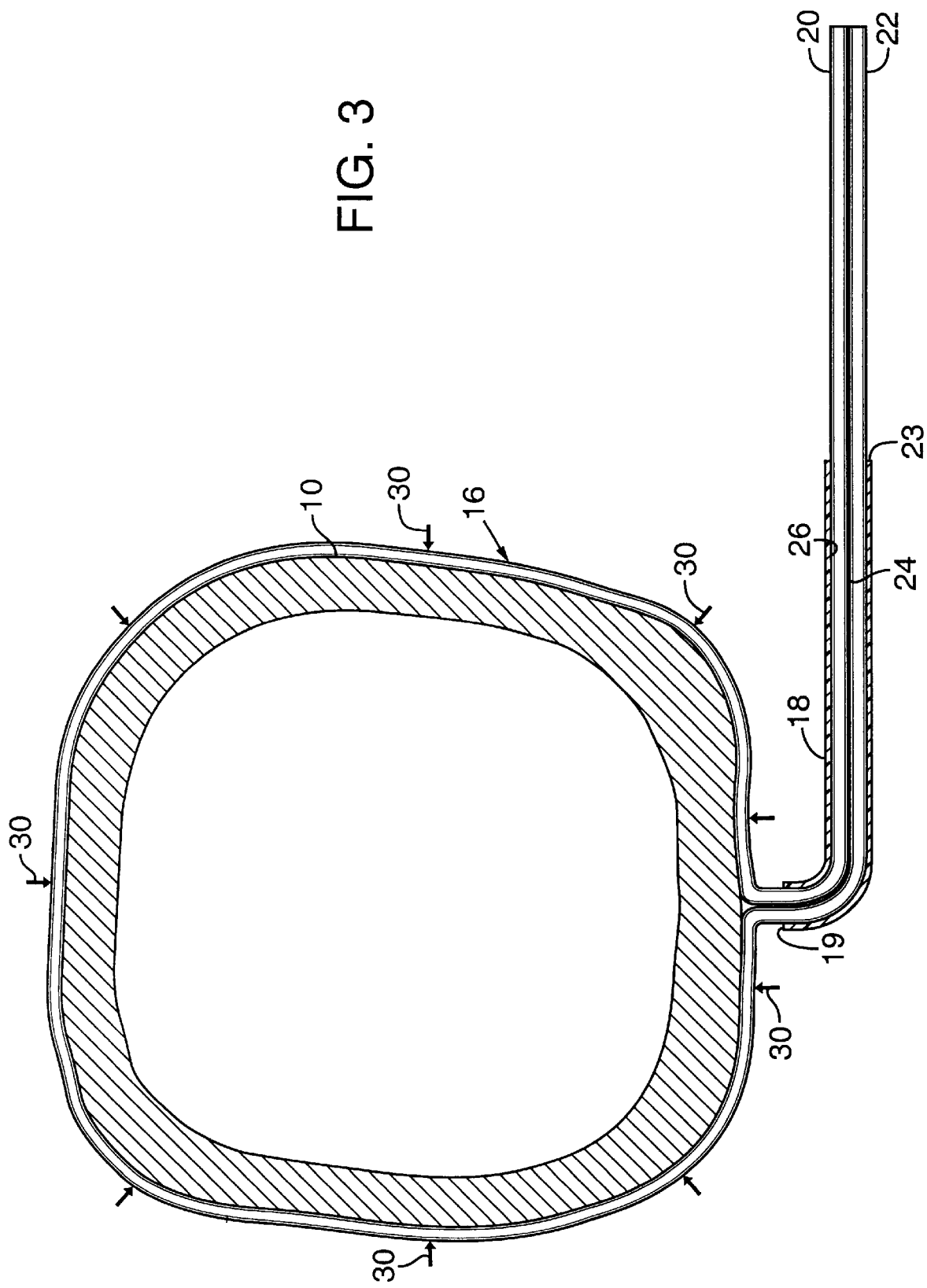
FIG. 3 is a top plan view of the tooth of FIG. 2 surrounded by an elastic gingival retraction loop after the loop has been closed around the tooth.

In addition, the preferred use of a flexible sleeve permits the sleeve to be bent, as shown in FIGS. 2 and 3 to minimize interference with the dental procedure, although the sleeve can remain straight or assume other shapes, if desired.

When an elastic gingival retraction cord is in a stretched condition around a tooth, it applies a slight continuous inwardly directed force around substantially the entire periphery of the tooth, as the cord is biased to return to its unstretched or relaxed length. This elasticity is distinguished from known gingival retraction cords which are composed of non-elastic thread weaved in a manner which provides some resilience but not elasticity. As previously explained, the use of elastic cord assists in seating the gingival retraction cord in the sulcus during use.

In FIG. 3, the elastic gingival retraction loop 16 has been pulled tightly around the base of the tooth 10 by pulling on the thread terminations 20 and 22 in a direction away from tooth 10. The arrows (some being numbered as 30) directed inwardly toward the center of the tooth indicate the compressive force which is exerted by the tightened gingival retraction loop 16 around the circumference of the prepared tooth 10. The portion of the loop 16 which abuts the tooth is represented by the dashed line in this figure because it can no longer be seen from the top view due to the configuration of the tooth.

Figure 4:
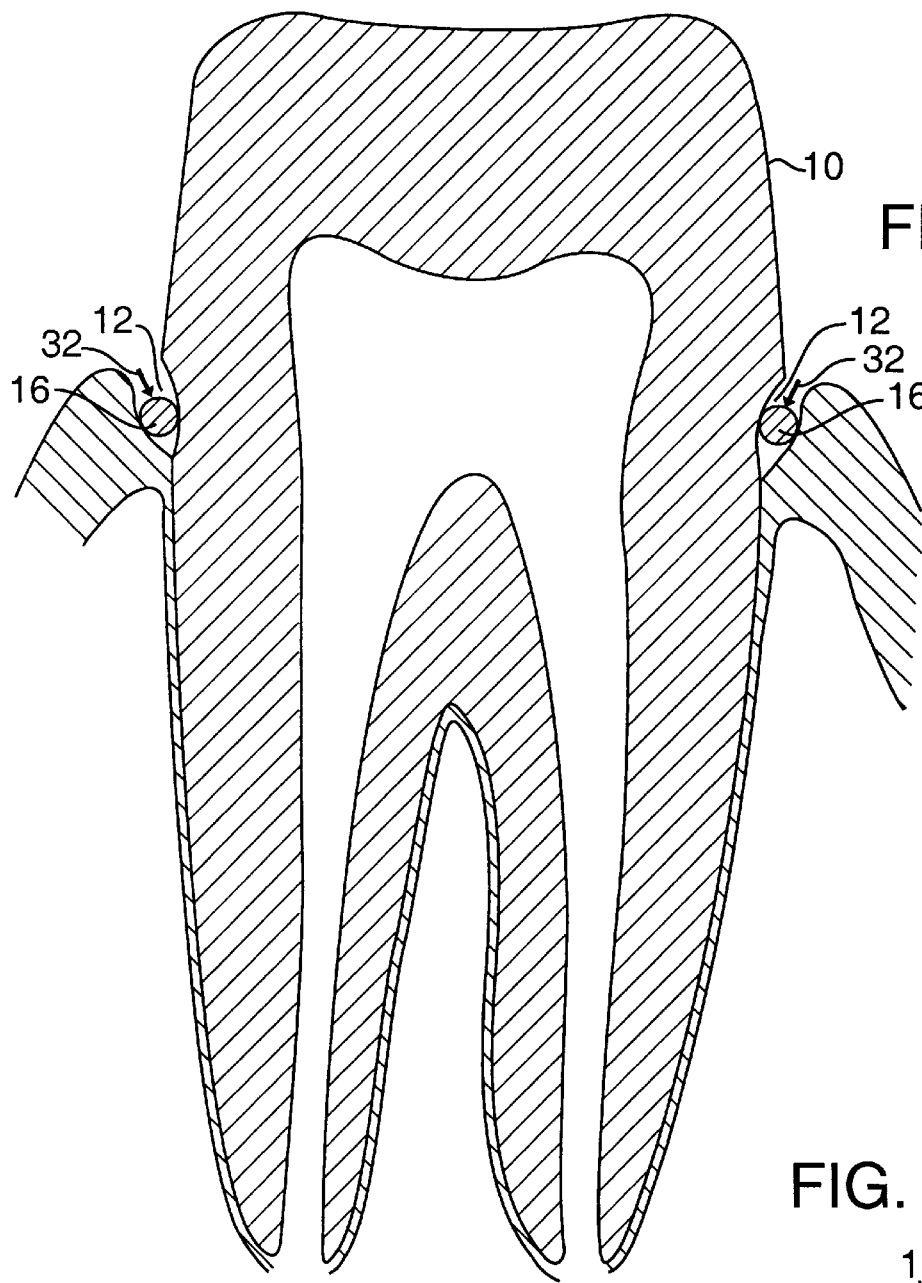
FIG. 4 shows, in vertical cross section, the tooth of FIG. 1 after the gingival retraction loop of FIG. 2 has been placed around the tooth and closed.

FIG. 4 shows the same vertical cross section seen in FIG. 1 with the elastic gingival retraction loop tightened in place around the neck of the tooth. The arrows 32 indicate the apical component of force exerted by the thread stretched around the circumference of the tooth. This component of force tends to seat the elastic thread at the bottom of the sulcus where retraction is most difficult. It can be seen that the sulcus 12 has been widened significantly and is now suitable for impression taking.

The illustrated embodiment of the present invention may be altered in arrangement and detail without departing from the principals of my invention. For example, although less preferred, elastic gingival retraction thread may be utilized with a different form of applicator or retainer to maintain the cord loop in its tightened condition. For example, a retainer stop or other device may be used to engage the cord ends to hold them after the loop is formed and tightened. As another example, the ends of the cord which pass through the sleeve may be inserted into a slit in the sleeve to retain the loop in a tightened state without using a heat shrunk sleeve. Also, a single end of the cord may be fixed to the sleeve or retainer, with the other end being free to be pulled to tighten the loop. However, the use of a monolithic sleeve of heat shrinkable material so as to frictionally engage an elastic gingival retraction loop is particularly advantageous as set forth above. I claim as my invention all such modifications which fall within the spirit and scope of the following claims.

I claim:

1. A method for retracting the gingival tissues from around the base of a tooth comprising:

placing a loop of elastic gingival retraction material around the tooth; and tightening the loop to close the loop and stretch the elastic gingival retraction material to generate an inwardly directed force against the tooth and to retract the gingival material.

2. A method according to claim 1 in which the tightening step comprises the step of stretching the elastic gingival retraction material around the entire circumference of the tooth so as to provide a uniform inwardly directed force against the entire periphery of the tooth, whereby, due to the tapered configuration of a typical tooth between its base and root, the force urges the elastic gingival retraction material to slide downwardly along the tapered portion of the tooth and into the space between the gingival tissues and the base of the tooth.

3. A method of claim 1 comprising the step of removing the loop following a dental procedure.

4. A method according to claim 1 in which the placing a loop step comprises:

placing around the base of the tooth a loop of gingival retraction material in the form of an elastic cord which passes through an elongated sleeve defining a cord passageway along its length, the loop having a loop forming portion which extends from the end of said elongated sleeve closest to the tooth and a tail forming portion comprising terminal ends of said loop of cord which extend beyond the end of said sleeve farthest from the tooth;

wherein the tightening the loop step comprises pulling on the tail forming portion of the loop so as to increase the length of the tail forming portion and correspondingly decrease the cross sectional dimension of the loop portion extending out of the end of said sleeve to thereby tighten the loop around a tooth; and frictionally engaging the cord passing through the sleeve to resist the sliding of the cord through the sleeve following the tightening of the loop step.

5. A method according to claim 4 wherein the step of frictionally engaging the cord comprises the step of reducing the cross-sectional dimension of the sleeve so that the interior of the sleeve frictionally engages the cord.

6. A method of forming a gingival retraction device comprising: providing an elongated sleeve with an elongated sleeve passageway having an interior cross-sectional dimension, the sleeve having first and second ends;

positioning gingival retraction cord into the sleeve passageway with a loop portion of the cord extending from the first end of the sleeve and a tail portion of the cord extending from the second end of the sleeve;

reducing the cross-sectional dimension of the passageway to restrict the ease at which the cord may be pulled through the sleeve to change the dimension of the loop, whereby upon tightening the loop around a tooth the loop remains in a tightened condition until removed; and in which the last named step comprises the step of heat shrinking the sleeve to reduce the cross-sectional dimension of the passageway to restrict the ease at which the cord may be pulled through the sleeve.

7. A method of forming a gingival retraction device comprising:

providing an elongated sleeve with an elongated sleeve passageway having an interior cross-sectional dimension, the sleeve having first and second ends;

positioning gingival retraction cord into the sleeve passageway with a loop portion of the cord extending from the first end of the sleeve and a tail portion of the cord extending from the second end of the sleeve;

reducing the cross-sectional dimension of the passageway to restrict the ease at which the cord may be pulled through the sleeve to change the dimension of the loop, whereby upon tightening the loop around a tooth the loop remains in a tightened condition until removed; and in which the gingival retaining cord comprises a material which is capable of being stretched in length at least five percent.

8. A method of forming a gingival retraction device comprising:

providing an elongated sleeve with an elongated sleeve passageway having an interior cross-sectional dimension, the sleeve having first and second ends;

positioning gingival retraction cord into the sleeve passageway with a loop portion of the cord extending from the first end of the sleeve and a tail portion of the cord extending from the second end of the sleeve;

reducing the cross-sectional dimension of the passageway to restrict the ease at which the cord may be pulled through the sleeve to change the dimension of the loop, whereby upon tightening the loop around a tooth the loop remains in a tightened condition until removed; and in which the gingival cord is of a material which is capable of being stretched in length at least from ten percent to fifty percent.

9. An apparatus for retracting the gingival tissues from around the base of a tooth comprising:

a loop formed of a gingival retraction cord, the loop having a first loop portion and a second tail portion, the second tail portion including at least one free end of the gingival retraction cord which is operable to reduce the cross sectional dimension of the loop when the loop is placed around the tooth and said at least one free end is pulled; and a one-piece monolithic loop retainer frictionally engaging the cord, the loop retainer being operable to retain the loop portion in the shape of a loop while permitting said at least one free end to be pulled to reduce the cross sectional dimension of the loop.

10. An apparatus according to claim 9 in which the loop retainer comprises an elongated sleeve having an internal axially extending passageway sized to receive and frictionally engage at least a portion of the cord so as to maintain the loop portion at a substantially constant cross sectional dimension following the pulling of said at least one free end.

11. An apparatus according to claim 9 in which the loop retainer comprises an elongated sleeve with first and second ends and a longitudinal axis, the sleeve having an axial cord passageway extending between the first and second ends, the loop being formed of a cord having first and second end portions, the cord being folded back upon itself to provide the loop portion and a tail portion comprised of the first and second end portions, the cord being inserted through the cord passageway with the loop portion projecting outwardly beyond the first end of the sleeve and the tail portion projecting outwardly beyond the second end of the sleeve, whereby pulling the tail portion away from the first end of the sleeve reduces the cross sectional dimension of the loop, and wherein the interior wall of the sleeve is sized to frictionally engage the cord passing therethrough.

12. An apparatus for retracting the gingival tissues from around the base of a tooth comprising:

a loop formed of a gingival retraction cord, the loop having a first loop portion and a second tail portion, the second tail portion including at least one free end of the gingival retraction cord which is operable to reduce the cross sectional dimension of the loop when the loop is placed around the tooth and said at least one free end is pulled; and a loop retainer frictionally engaging the cord, the loop retainer being operable to retain the loop portion in the shape of a loop while permitting said at least one free end to be pulled to reduce the cross sectional dimension of the loop; and in which the gingival cord comprises an elastic material capable of stretching in length at least from ten percent to fifty percent.

13. An apparatus for retracting the gingival tissues from around the base of a tooth comprising:

a loop formed of a gingival retraction cord, the loop having a first loop portion and a second tail portion, the second tail portion including at least one free end of the gingival retraction cord which is operable to reduce the cross sectional dimension of the loop when the loop is placed around the tooth and said at least one free end is pulled; and a loop retainer frictionally engaging the cord, the loop retainer being operable to retain the loop portion in the shape of a loop while permitting said at least one free end to be pulled to reduce the cross sectional dimension of the loop; and in which the gingival cord comprises an elastic material capable of stretching in length at least five percent.

14. An apparatus for retracting the gingival tissues from around the base of a tooth comprising:

a loop formed of a gingival retraction cord, the loop having a first loop portion and a second tail portion, the second tail portion including at least one free end of the gingival retraction cord which is operable to reduce the cross sectional dimension of the loop when the loop is placed around the tooth and said at least one free end is pulled; and a loop retainer frictionally engaging the cord, the loop retainer being operable to retain the loop portion in the shape of a loop while permitting said at least one free end to be pulled to reduce the cross sectional dimension of the loop;

in which the loop retainer comprises an elongated sleeve with first and second ends and a longitudinal axis, the sleeve having an axial cord passageway extending between the first and second ends, the loop being formed of a cord having first and second end portions, the cord being folded back upon itself to provide the loop portion and a tail portion comprised of the first and second end portions, the cord being inserted through the cord passageway with the loop portion projecting outwardly beyond the first end of the sleeve and the tail portion projecting outwardly beyond the second end of the sleeve, whereby pulling the tail portion away from the first end of the sleeve reduces the cross sectional dimension of the loop, and wherein the interior wall of the sleeve is sized to frictionally engage the cord passing therethrough; and in which the sleeve is of a heat shrinkable material and is heat shrunk to size the interior wall of the sleeve to frictionally engage the cord.

15. A device for retracting the gingival tissues from around the base of a tooth comprising:

an elongated sleeve having first and second ends and an interior wall defining a cord passageway along the length of the sleeve;

a length of elastic cord having first and second ends folded over to form a loop, said loop extending outwardly from a first end of said elongated sleeve, through the cord passageway, and the free ends of said length of cord extending outwardly through the second end of said elongated sleeve, whereby pulling the free ends of said cord through said cord passageway reduces the cross sectional dimension of said loop and tightens said loop around the base of the tooth; and means for holding said cord in order to prevent it from sliding back through said cord passageway after the loop has been tightened around the base of the tooth.

16. The apparatus of claim 15 wherein the means for holding said cord comprises a section of the interior wall which defines an internal cord passageway which is sized to compress said cord.

17. The apparatus of claim 16 wherein said sleeve is comprised of a heat shrinkable material which is heat shrunk to size the cord passageway to compress said cord.

18. The apparatus of claim 15 wherein the elastic cord contains an absorbent component for carrying medicaments for the gingival tissue.

19. An apparatus for retracting the gingival tissues from around the base of a tooth comprising:

a loop formed of an elastic gingival retraction cord which is capable of being stretched in length at least five percent;

an elongated loop retainer sleeve having the loop projecting outwardly from the sleeve and a length of the loop cord positioned within the sleeve, whereby the cross sectional dimension of the loop may be reduced with the loop positioned around the tooth to retract the gingival tissue from around the base of the loop.

* * * * *